United States Patent
Froggatt et al.

(10) Patent No.: US 10,480,926 B2
(45) Date of Patent: Nov. 19, 2019

(54) APPARATUS AND METHOD FOR GENERATING 3-D DATA FOR AN ANATOMICAL TARGET USING OPTICAL FIBER SHAPE SENSING

(71) Applicant: Intuitive Surgical Operations, Inc., Sunnyvale, CA (US)

(72) Inventors: Mark E. Froggatt, Blacksburg, VA (US); Eric E. Sanborn, Blacksburg, VA (US); Federico Barbagli, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/757,436

(22) PCT Filed: Dec. 8, 2016

(86) PCT No.: PCT/US2016/065596
§ 371 (c)(1),
(2) Date: Mar. 5, 2018

(87) PCT Pub. No.: WO2017/106003
PCT Pub. Date: Jun. 22, 2017

(65) Prior Publication Data
US 2018/0245907 A1    Aug. 30, 2018

Related U.S. Application Data

(60) Provisional application No. 62/266,879, filed on Dec. 14, 2015.

(51) Int. Cl.
*G01B 9/02*     (2006.01)
*G01M 11/00*    (2006.01)
(Continued)

(52) U.S. Cl.
CPC ........... *G01B 9/0209* (2013.01); *A61B 3/102* (2013.01); *A61B 3/107* (2013.01); *A61B 5/0066* (2013.01);
(Continued)

(58) Field of Classification Search
USPC ........................................ 356/482, 479, 497
See application file for complete search history.

(56) References Cited

U.S. PATENT DOCUMENTS 8,773,650 B2    7/2014 Froggatt et al.
2009/0324161 A1  12/2009 Prisco
(Continued)

FOREIGN PATENT DOCUMENTS

WO    WO-2014100291 A1    6/2014
WO    WO-2014204839 A1    12/2014

OTHER PUBLICATIONS

International Search Report and Written Opinion for Application No. PCT/US2016/065596, dated Mar. 24, 2017, 11 pages.
(Continued)

*Primary Examiner* — Kara E. Geisel
*Assistant Examiner* — Jonathon Cook
(74) *Attorney, Agent, or Firm* — Schwegman Lundberg & Woessner, P.A.

(57) ABSTRACT

A fiber housing includes multiple shape sensing cores and a single optical core. A distal end of the fiber housing is positionable to direct the single optical core to a current point of an anatomical target. Collimated light over a first range of frequencies is projected from the single optical core to the current point. OFDR is used to detect reflected light scattered from the current point and to process the detected light to determine a distance to the current point. Light over a second range of frequencies is projected through the multiple shape sensing optical cores to the distal end of the
(Continued)

fiber housing. OFDR is used to measure light reflected from the distal end of the fiber housing back through the multiple shape sensing optical cores and to process the measurement to determine a position in three dimensional space of the distal end of the fiber housing and a pointing direction of the distal end of the fiber housing. A position in three dimensional space of the current point is determined based on the determined position in three dimensional space of the distal end of the fiber housing, the pointing direction of the distal end of the fiber housing, and the determined distance.

20 Claims, 15 Drawing Sheets

(51) Int. Cl.
    *A61B 3/10*     (2006.01)
    *A61B 5/00*     (2006.01)
    *A61B 3/107*     (2006.01)
    *A61B 5/026*     (2006.01)
    *A61B 5/1459*     (2006.01)
    *A61B 5/06*     (2006.01)
    *A61B 5/107*     (2006.01)
(52) U.S. Cl.
    CPC ............ *A61B 5/0261* (2013.01); *A61B 5/061* (2013.01); *A61B 5/1072* (2013.01); *A61B 5/1076* (2013.01); *A61B 5/1459* (2013.01); *G01M 11/3172* (2013.01)

(56) References Cited

U.S. PATENT DOCUMENTS

| | | |
|---|---|---|
| 2011/0157552 A1* | 6/2011 | Bublitz ................ A61B 3/1005 351/209 |
| 2012/0323075 A1 | 12/2012 | Younge et al. |
| 2013/0085330 A1 | 4/2013 | Ramamurthy et al. |
| 2014/0160484 A1* | 6/2014 | Kang ................ G01B 9/02045 356/479 |
| 2014/0180075 A1 | 6/2014 | Kulkarni et al. |
| 2014/0257095 A1* | 9/2014 | Kemp ...................... A61B 8/12 600/427 |
| 2014/0320846 A1 | 10/2014 | Froggatt et al. |
| 2016/0015468 A1* | 1/2016 | Piron ................... A61B 5/6847 600/424 |
| 2016/0206384 A1* | 7/2016 | Dimaio ................. A61B 34/20 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 16876412.4 dated May 13, 2019, 9 pages.

* cited by examiner

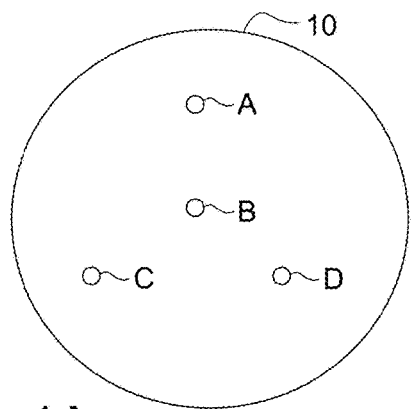
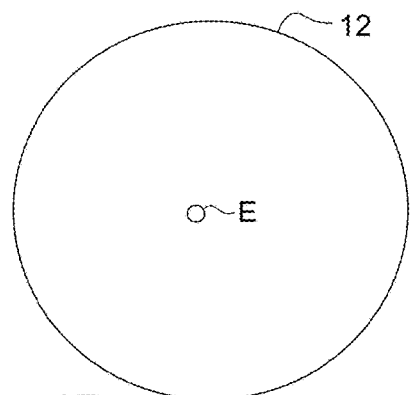
Fig. 1A            Fig. 1B
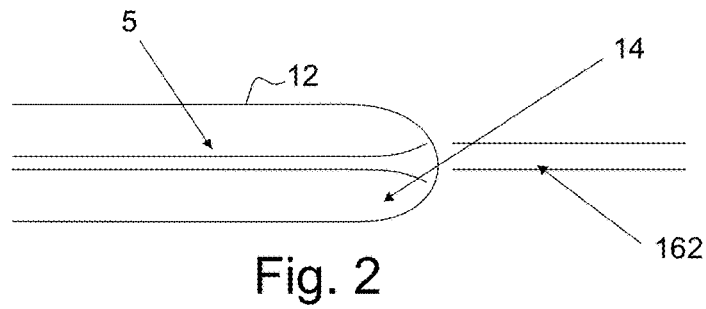
Fig. 2
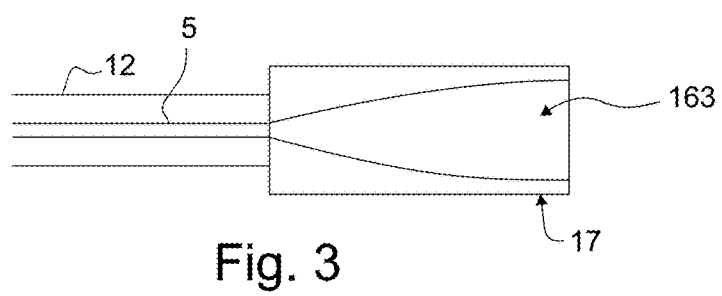
Fig. 3
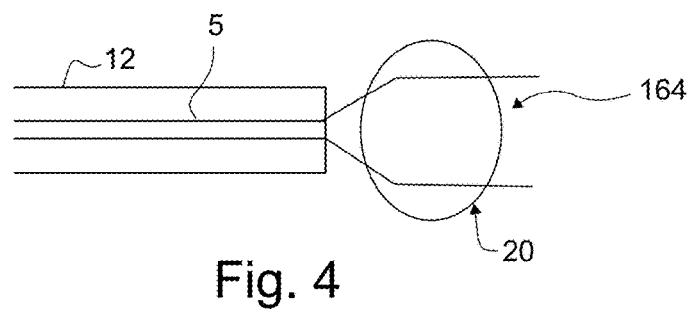
Fig. 4

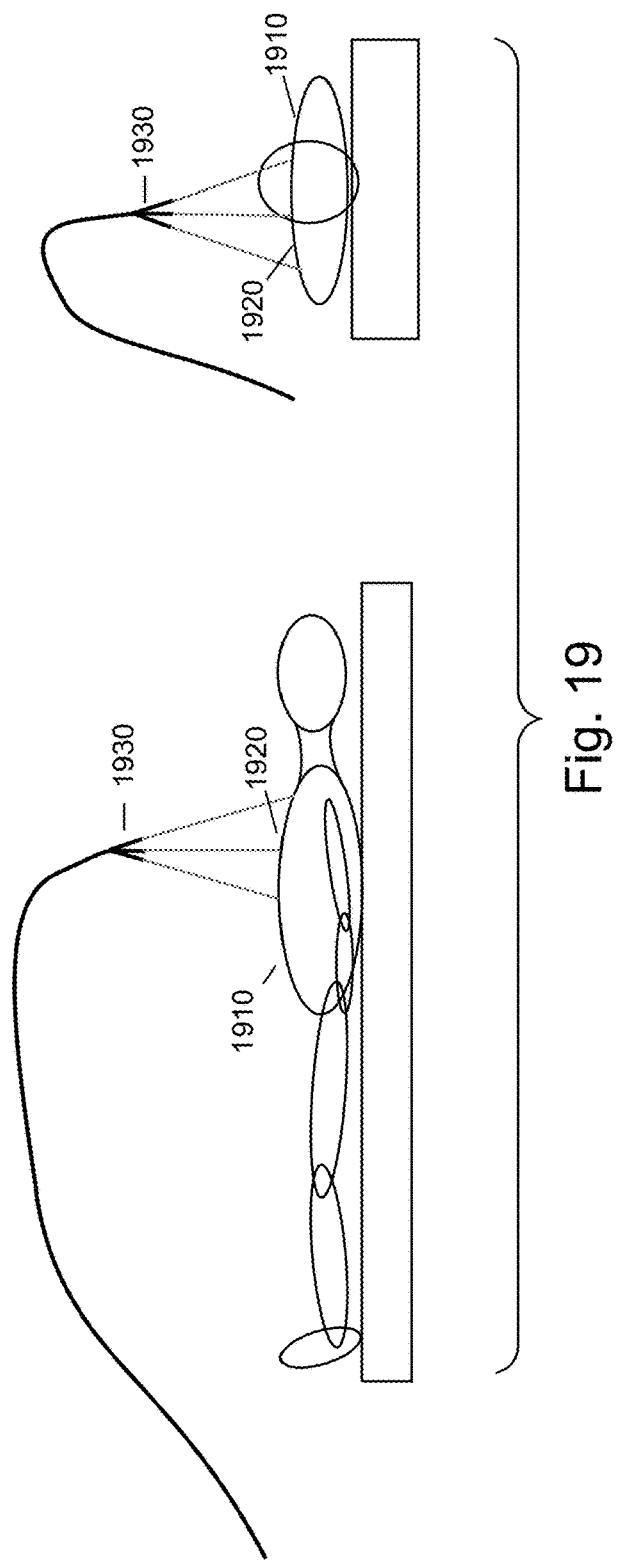

US 10,480,926 B2

APPARATUS AND METHOD FOR GENERATING 3-D DATA FOR AN ANATOMICAL TARGET USING OPTICAL FIBER SHAPE SENSING

RELATED APPLICATIONS

This application is the U.S. national phase of International Application No. PCT/US2016/065596 filed Dec. 8, 2016, which designated the U.S. and claims benefit to U.S. Provisional Patent Application 62/266,879, entitled "APPARATUS AND METHOD FOR GENERATING 3-D DATA FOR AN ANATOMICAL TARGET USING OPTICAL FIBER SHAPE SENSING," filed Dec. 14, 2015, the entire contents of each of which are hereby incorporated by reference.

TECHNICAL FIELD

The technology relates to optical fiber position sensing based on interferometric measurements to provide position and orientation information.

INTRODUCTION

Optical strain sensing is useful for measuring physical deformation of an optical fiber caused by, for example, the change in tension, compression, or temperature of the optical fiber. A multi-core optical fiber is composed of several independent waveguides or cores embedded within a single fiber. A continuous measure of strain along the length of a core can be derived by interpreting the optical response of the core using swept wavelength inteferometry. With knowledge of the relative positions of the cores along the length of the fiber, these independent strain signals may be combined to gain a measure of a strain profile applied to the multi-core optical fiber. The strain profile of the fiber is a measurement of applied bend strain, twist strain, and/or axial strain along the length of the fiber at a high (e.g., less than 50 micrometers) sample resolution. In a technique known as optical position and/or shape sensing detailed in commonly-assigned U.S. Pat. No. 8,773,650 to Froggatt et al., entitled "Optical Position and/or Shape Sensing," which is incorporated herein by reference, this strain profile information is used to reconstruct the three dimensional position of the fiber.

A tomographic optical system obtains virtual "slices" (a tomographic image) of specific cross-sections of a scanned object. These virtual slices allows a user to see inside an object (e.g., a human anatomical target) without physically cutting it. Tomography involves gathering projection data from multiple directions either transmitted through or reflected from an anatomical target. That projection data is then processed by a reconstruction algorithm to generate the virtual slices. Unfortunately, known tomography approaches require that each of the transmitter locations and detector locations is known with a high degree of accuracy and precision.

Commonly used forms of tomography include CAT scans, PET scans, and MRI scans. For example, CAT scans use multiple x-ray detectors at different locations to measure x-rays from x-ray transmitters located at many different positions. Since the CAT scan machine is large and outside of the anatomical target, it is a relatively easy task to determine the coordinates of these different positions very accurately and precisely.

Optical coherence tomography (OCT) uses visible or near-IR light instead of x-rays and uses reflected light instead of transmitted light. OCT, however, does not penetrate deeply into tissue, and typically, can only scan to a depth on the scale of millimeters, e.g., a few millimeters to a few centimeters. As a result of scanning depth limitations, it is necessary to place OCT probes inside an anatomical target in order to effectively scan tissue inside an anatomical target cavity. It would be desirable to be able to perform OCT scanning at greater depths. It would also be useful to have a greater OCT measuring range so that the surface of tissue can be located and probed from a distance.

Still further, it would be useful to be able to perform topographic measurements where the exterior surface of an anatomical target cavity (such the abdomen, lung, mouth, throat, nose, or ears) is measured. These measurements could then be used to register previously taken CAT scans (or PET scans or MRI scans) to a coordinate frame in which a surgeon is working to provide an "overlay" of the CAT scan image with the currently visible tissue Although the distance of a reflection from an OCT source and the relative angle between measurements as a mirror is scanned or a fiber is rotated can be determined, it is difficult to determine the absolution position and angle of the source. Machines such as a "FaroArm" use multiple hinged segments with high-resolution encoders to measure three dimensional locations and angles. But FaroArm machines, like CAT, PET, and MRI machines, are too large to be placed inside a human anatomical target and are even too intrusive to be used outside of the anatomical target in an operating room.

SUMMARY

The inventors recognized that shape sensing fiber and a fiber shape measurement system can be used to provide the desired measurements identified in the introduction with a high degree of accuracy using a small, inexpensive, and unobtrusive device (e.g., a 200 micron diameter optical fiber). The technology described in this application uses shape sensing fiber and a fiber shape measurement system to generate information concerning the distribution of tissue at and around an area in which a surgeon is operating. The technology may also perform three dimensional scanning outside and/or inside an anatomical target to map tissue surfaces and/or identify sub-surface features.

In example embodiments, a fiber housing includes multiple shape sensing cores and a single optical core. A distal end of the fiber housing is positionable to direct the single optical core to a current point of an anatomical target. The current point may be in or on the anatomical target. Collimated light from the single optical core is projected over a first range of multiple frequencies to the current point. Optical frequency domain reflectometry (OFDR) is used to detect reflected light scattered from the current point and to process the detected light to determine a distance to the current point. Light is projected over a second range of multiple frequencies through the multiple shape sensing optical cores to the distal end of the fiber housing. OFDR is used to measure light reflected from the distal end of the fiber housing back through the multiple shape sensing optical cores and to process the measured light to determine a position in three dimensional space of the distal end of the fiber housing and a pointing direction of the distal end of the fiber housing. The determined position in three dimensional space of the distal end of the fiber housing, the pointing direction of the distal end of the fiber housing, and the determined distance are used to determine a position in three dimensional space of the current point.

The pointing direction of the distal end of the fiber housing may be expressed as a unit vector pointing in a direction of the distal end of the fiber housing to along a pointing axis. The unit vector is multiplied by the determined distance to generate a reflection distance vector, and the determined position in three dimensional space of the distal end of the fiber housing is combined with the reflection distance vector to generate the determined position in three dimensional space of the current point.

In an example implementation, the fiber housing includes a collimator for collimating light for the single optical core. A time delay from a reflection at the collimator to a first reflection scattered from the current point indicates the distance from the distal end of the fiber housing to the current point.

In example implementations, the multiple cores and the single core are in the same fiber or in different fibers.

In an example implementation, the multiple cores and the single core are fixed in a known positional relationship with each other.

In an example implementation, a three dimensional data set for at least a portion of the anatomical target is generated by directing the distal end of the fiber housing at different current points and repeating the steps described above for each current point. For one example application, the data set is generated for a cavity in a human or animal, in which case, the three dimensional data set provides information about a distribution of tissue of an area in the anatomical target in which a surgeon is operating. Furthermore, a tomographical map may be generated of at least a portion of a surface of the anatomical target and/or beneath a surface of the anatomical target based on the three dimensional data set. Yet another application is to use the three dimensional data set to navigate a cavity in the anatomical target.

Another aspect of the technology in example embodiments includes detecting relative optical phase shifts in the reflected light caused by motion of anatomical target tissue and compensating the three dimensional data set for motion of anatomical target tissue based on the detected optical phase shifts.

Another aspect of the technology in example embodiments includes determining a position in three dimensional space of points on the outside of the anatomical target to determine the location of the anatomical target in three dimensional space, and using the determined location of the outside of the anatomical target in three dimensional space and a radiation-based scan of the anatomical target to determine a location of one or more structures inside the anatomical target in three dimensional space. For example, the radiation-based scan is a CAT, PET, or MRI scan.

Another example embodiment relates to an interferometric measurement system having a fiber housing that includes multiple shape sensing cores and a single optical core. A distal end of the fiber housing is positionable to direct the single optical core to a current point in or on an anatomical target. The system includes a tunable light source that projects, over a range of multiple frequencies, light through the single optical core and a collimator to the current point. The system also includes circuitry that detects reflected light scattered from the current point and to process the detected light to determine a distance to the current point using optical frequency domain reflectometry (OFDR). The tunable light source projects light over a range of multiple frequencies through the multiple shape sensing optical cores to the distal end of the fiber housing. The circuitry measures light reflected from the distal end of the fiber housing back through the multiple shape sensing optical cores and processes the measurement to determine a position in three dimensional space of the distal end of the fiber housing and a pointing direction of the distal end of the fiber housing using OFDR. Ultimately, the circuitry determines a position in three dimensional space of the current point based on the determined position in three dimensional space of the distal end of the fiber housing, the pointing direction of the distal end of the fiber housing, and the determined distance.

BRIEF DESCRIPTION OF THE DRAWINGS

FIG. 1A shows an example cross section of a multi-core shape sensing fiber;

FIG. 1B shows an example cross section of a single-core distance or range sensing fiber;

FIGS. 2-4 are diagrams illustrating example collimators;

FIG. 19 shows another example application of the OFDR-based tomography technology to determine a location of an anatomical target in space.

DETAILED DESCRIPTION

Figure 5:
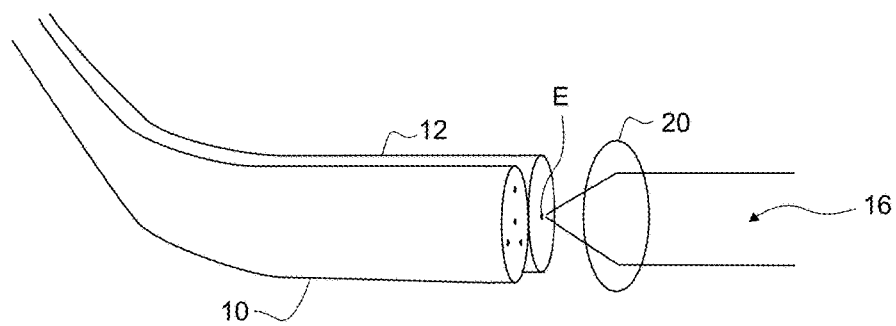
FIG. 5 shows an example of a multi-core shape sensing fiber positioned with a single-core distance sensing fiber ("the fiber pair")

The technology described in this application provides three dimensional scanning inside and/or outside a human, animal, or other organic or inorganic anatomical target using a paired shape sensing fiber and single-core fiber. The shape sensing fiber provides position and orientation information, and the single-core fiber provides distance or range information to the point(s) on or in the anatomical target being scanned.

The shape sensing fiber allows for the precise determination of the location and pointing direction of the single-core fiber optical transmitter inside or outside an anatomical target using optical frequency domain reflectometry (OFDR) technology. The single-core fiber optical transmitter includes a collimator at its transmitting (distal) end and provides a distance to a current point in or on the anatomical target from light back-scattered into the collimator and processed using OFDR. The position of the current point in or on the anatomical target in three dimensions can be obtained because both the three dimensional position and pointing direction (which can be expressed as a pointing angle, through some other measurement, etc.) of the single-core fiber optical transmitter are known from the shape sensing fiber and the distance from the fiber tip to a current point in or on the anatomical target is known from the single-core fiber. An example reflection-based tomography embodiment of this technology is now described.

FIG. 1A shows an example cross section of a multi-core shape sensing fiber 10 including four optical cores A-D with core B being a center core and cores A, C, and D spaced around core B. FIG. 1B shows an example cross section of a single-core distance or range sensing fiber 12 with a single optical core E.

The single core E may be paired with the multiple cores A-D by including it within the shape sensing fiber 10, such as near the core B or elsewhere in the shape sensing fiber 10. In some instances, the single core E may be included in its own fiber 12 that is positioned next to the shape sensing fiber 10 in use. An example situation that favors the former approach that includes core E in shape sensing fiber 10 is where an integrated fiber is desired for physical dimensions, for alignment between the cores A-E, to provide one fiber to the user of the system, etc. An example situation that favors the latter pairing that configures core E in a fiber 12 separate from cores A-D in a fiber 10 is when it is preferred for optics for core E; for example, in some embodiments, it can be difficult to provide an acceptable termination at the end of the shape sensing fiber 10 when the single core E has, or is configured with, collimating optics. Example embodiments below assume a two fiber pair in discussion for ease of description, and these techniques are also applicable to single fiber embodiments.

To perform the distance/ranging measurement provided by the single core E, an example embodiment collimates the light transmitted and received at the distal/pointing end of the single core E. Light collimation may be accomplished in a number of ways. One example is shown in FIG. 2 where the end of the fiber 12 is melted and allowed to form a curved surface 14 approximating a convex lens that tends to collimate the light (collimated beam 162). This collimator embodiment is inexpensive, easy, and small, but not necessarily as effective as other collimators and may or may not be sufficient for particular applications depending on the details of the lens formation process.

FIGS. 3 and 4 illustrate example collimators of which some embodiments may be more effective than the one for the example shown in FIG. 2. FIG. 3 shows a micro GRIN (gradient-index) lens 17 collimator with its collimated beam 163, and FIG. 4 shows a ball-lens-type collimator 20 with its collimated beam 164.

The single-core fiber 12 may be bonded, for example, to the multicore shape sensing fiber 10 at their respective ends such that all six degrees of freedom (x, y, z, roll, pitch, and yaw) of the single-core fiber 12 may be determined from the multicore shape sensing fiber 10 to provide the position and pointing direction (e.g. as a pointing angle, some other measurement, etc.) of the distal end. FIG. 5 shows an example of a multi-core shape sensing fiber positioned together with a single-core fiber 12 having a collimator 20. Together they are referred to as the fiber pair.

Figure 6:
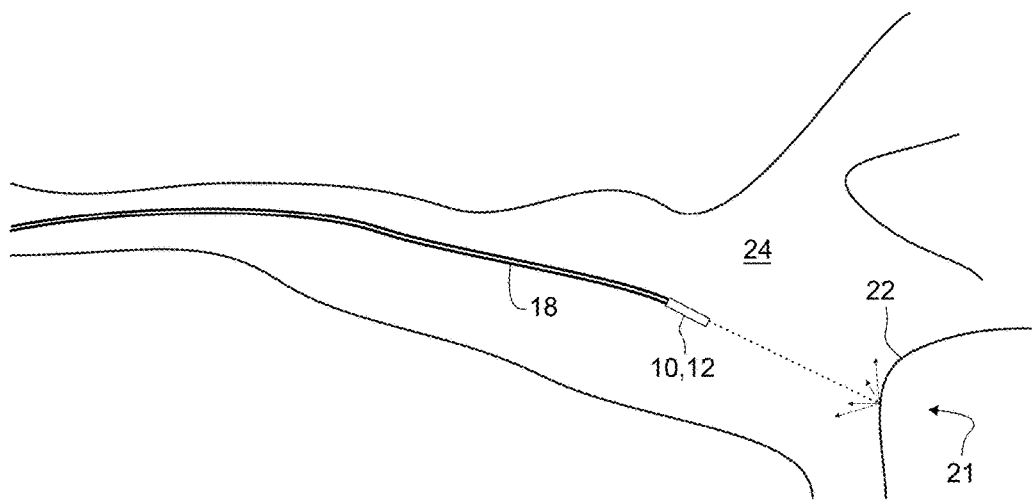
FIG. 6 shows an example of the fiber pair embedded inside a fiber housing positioned inside an anatomical target.

In one example embodiment, the paired fibers 10 and 12 are embedded in a fiber housing that is inserted into a cavity inside of an anatomical target. FIG. 6 shows an example. The two fibers 10 and 12 are included inside of a fiber housing 18, positioned inside a cavity 24 of an anatomical target 21. Examples of fiber housing 18 include a catheter, a lumen of the catheter, a non-catheter housing, and the like. The light exiting the single-core fiber 12 with collimation encounters an interior anatomical target surface 22 at a current point and scatters. Some of the scatter will be Lambertian (omnidirectional), and a portion of this light scatters back into the collimating optics associated with the fiber 12 and travels back through the single core E of the fiber 12. Although losses may be negligible or significant, OFDR is very sensitive, and the sensing system can be designed such that back scatter is sufficient to resolve the anatomical target surface or sub-surface using OFDR.

Figure 7:
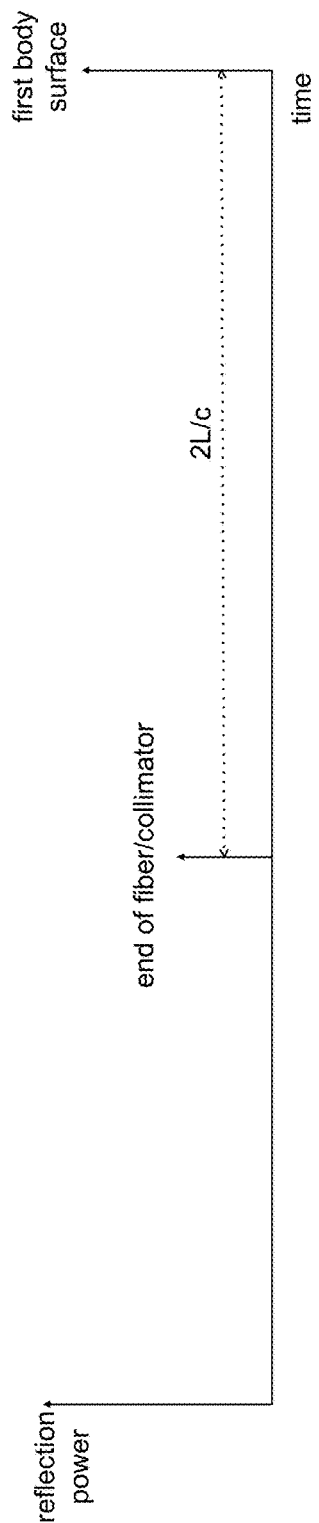
FIG. 7 illustrates a graph of a time domain response of light sent through a single-core fiber and into the anatomical target.

FIG. 7 illustrates an example graph of a time domain response of light sent through the single core fiber 12 and into the anatomical target 21. The time delay from the reflection at the collimator 20 to the first large reflection is an indication of the distance from the end of the single core fiber 12 to the first anatomical target surface. The speed of light in air "c" is used to convert the measured round trip time delay into the distance L from the distal end of the single core fiber 12 to the first tissue surface, where the delay=2L/c, c being the speed of light.

Figure 8:
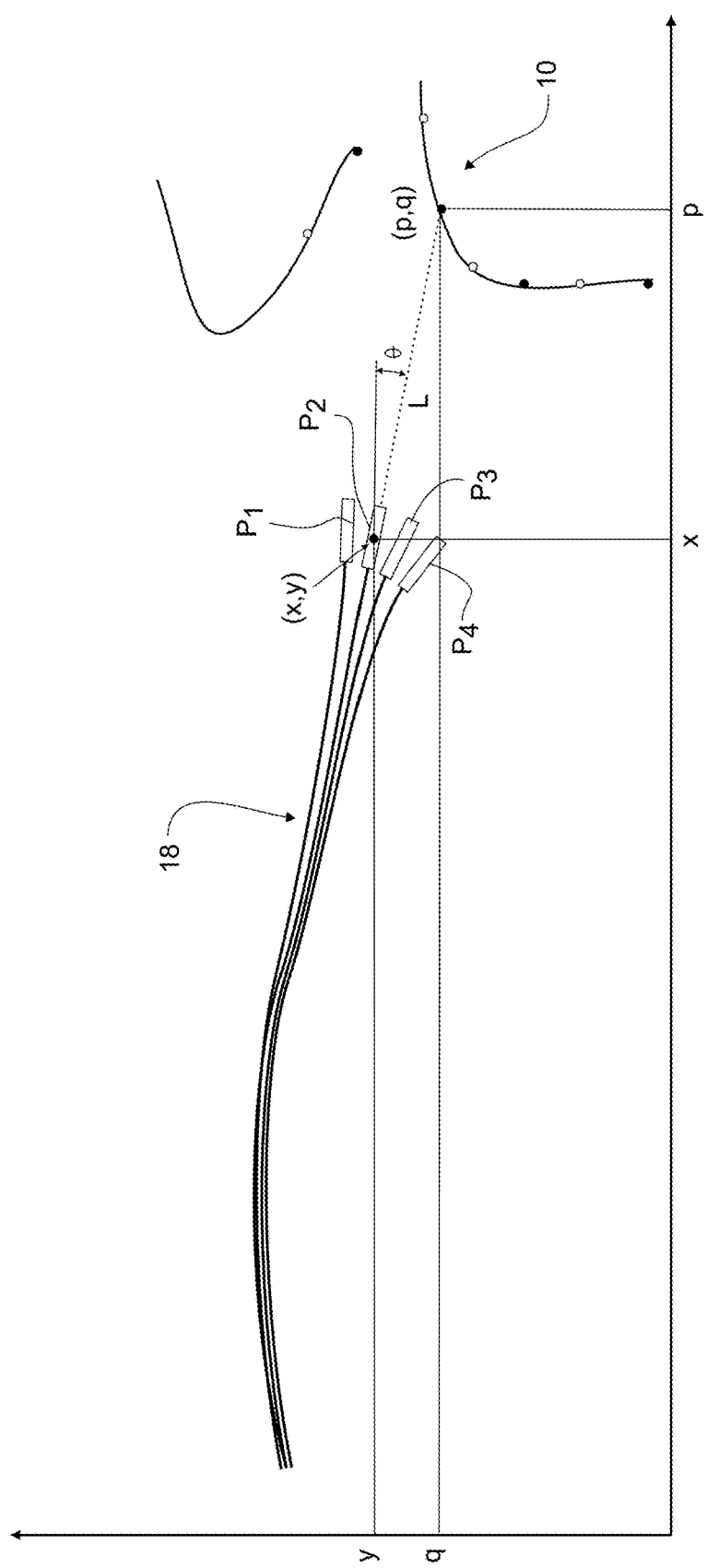
FIG. 8 illustrates in a two-axis plane an example determination of a reflection point on the surface of the anatomical target using coordinate and orientation information from the multicore shape sensing fiber and the single-core collimated fiber.

FIG. 8 illustrates in a two-axis coordinate plane an example determination of a reflection point on the surface 22 of the anatomical target using: coordinate and orientation information from the multicore shape sensing fiber 10, and distance information from the single core fiber 12. The illustration of FIG. 8 is similar to a two-dimensional mapping of the example shown in FIG. 6. The position and angle of the single core fiber 12 tip (distal end) can be determined using the shape sensing fiber 10 and the distance from the fiber pair tip to the reflecting point (p,q). The position and angle information of the single core fiber 12 tip can be used in determining the location in space of the reflecting point in the anatomical target. In FIG. 8, the fiber housing 18 is shown moved to four different positions P1-P4 in a scan operation. An actuator such as a robotic arm (e.g., see robotic arm 104 of FIG. 18) may be controlled to move the fiber housing 18 into the anatomical target cavity 24 and to point the tip of the fiber housing 18 at the different positions P1-P4. Pointing position P2 has a vertical coordinate y and a horizontal coordinate x. A pointing direction is expressed as a pointing angle θ in the x-y plane, and the length from the tip of the fiber housing 18 to the current point p, q on the surface 22 of the anatomical target is shown as L. In various embodiments, θ is determined from information obtained from the shape sensing fiber 10, and L is determined as discussed above in conjunction with FIG. 7.

Figure 9:
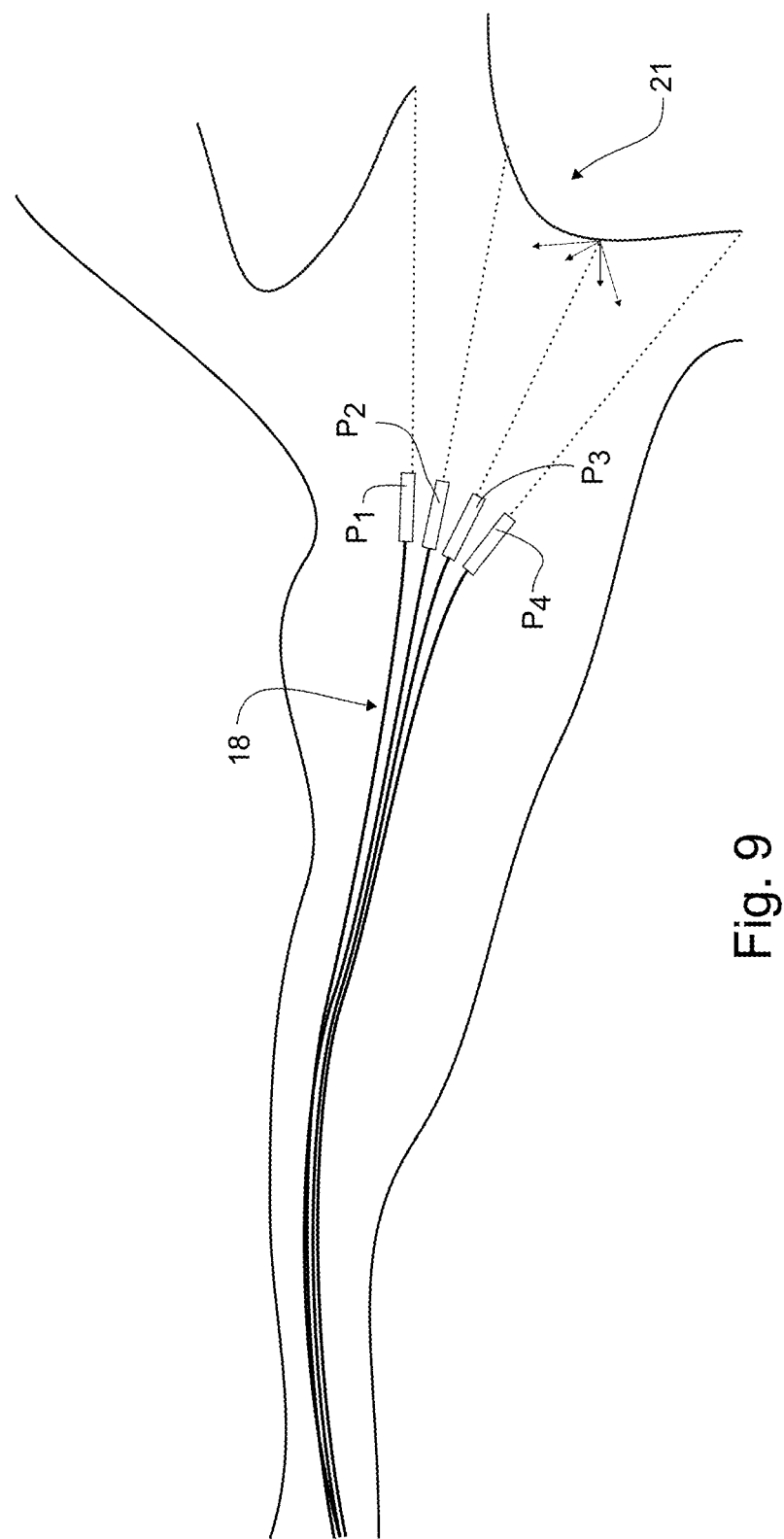
FIG. 9 shows multiple positions and orientations of a fiber housing tip used to locate multiple points on the anatomical target surface in an embodiment.

FIG. 9 is like FIG. 8 and shows multiple positions P1-P4 and orientations of the fiber housing 18 tip used to locate multiple points on interior target surface 22 of the anatomical target 21.

Appropriate scanning the fiber housing 18 tip through different positions and angles generates a three dimensional data set of the scattering surface(s). The three dimensional data set of the scattering surface(s) may be used to generate a three dimensional map of those surface(s) and/or may be used for navigation inside the anatomical target 21.

Figure 10:
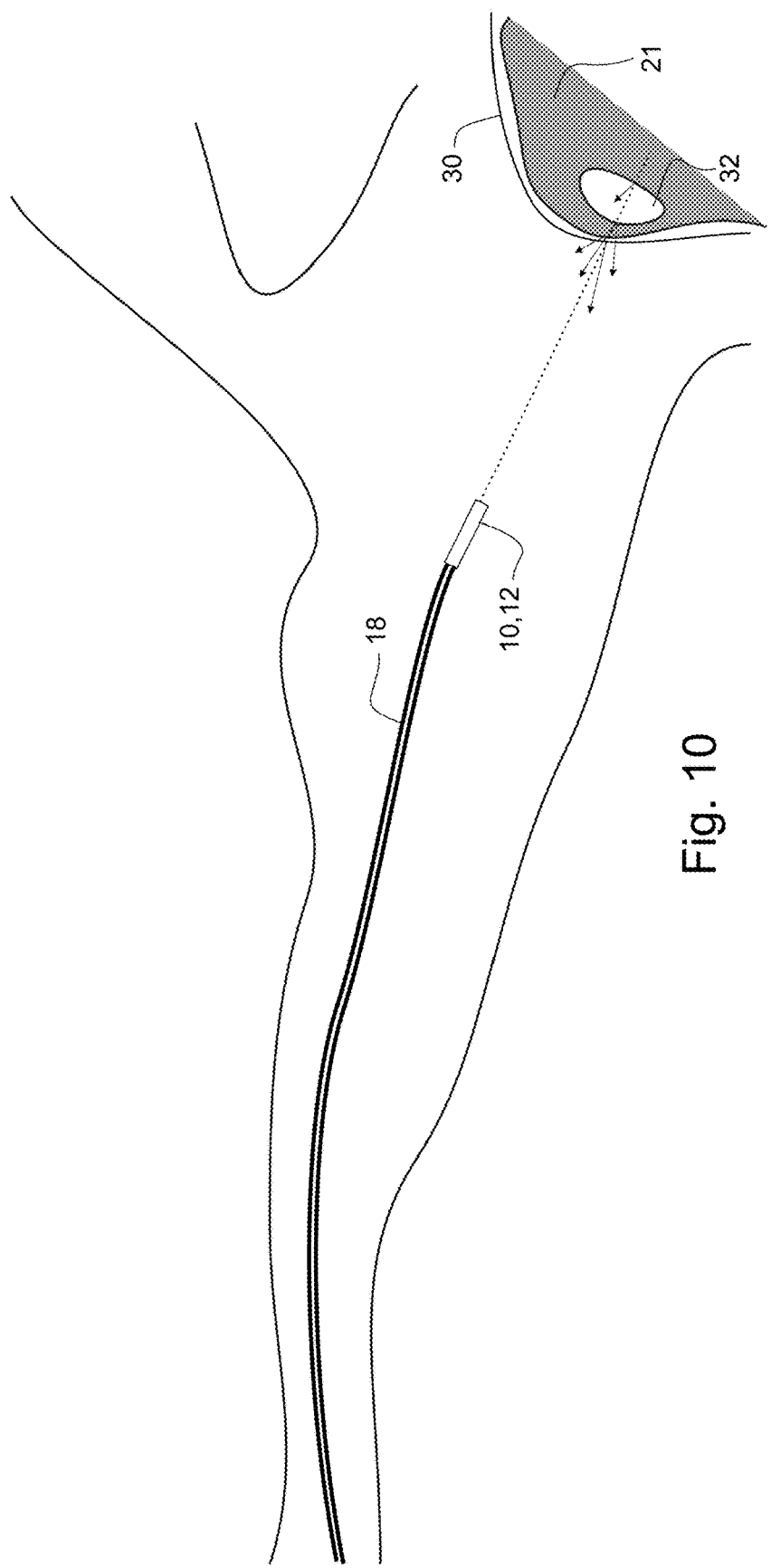
FIG. 10 illustrates an example of scatter from surface and subsurface features of the anatomical target.
Figure 11:
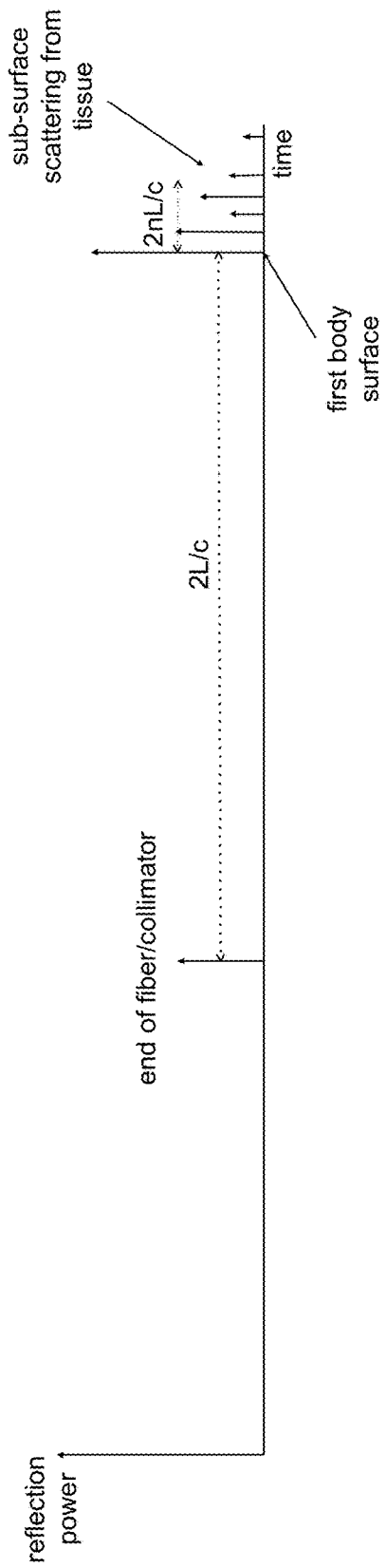
FIG. 11 is an example graph of reflection power v. time delay showing an example of reflections and optical path delay/distance.

FIG. 10 illustrates an example of scatter from surface 30 and subsurface 32 features of the anatomical target 21. A time domain reflection graph of reflection power v. time delay shown in FIG. 11 shows detected subsurface scattering beyond the initial tissue surface 30. In various embodiments, light with a wavelength of 1 micron should be able to penetrate several millimeters into the anatomical target tissue and can be used to determine the anatomy beneath the scanned surface 30. Maps of sub-surface features may be generated using a process similar to the process used to find the tissue surface while also accounting for the index of refraction differences within the tissue which cause the collimated beam to refract (bend) and changes the speed of light.

Figure 12:
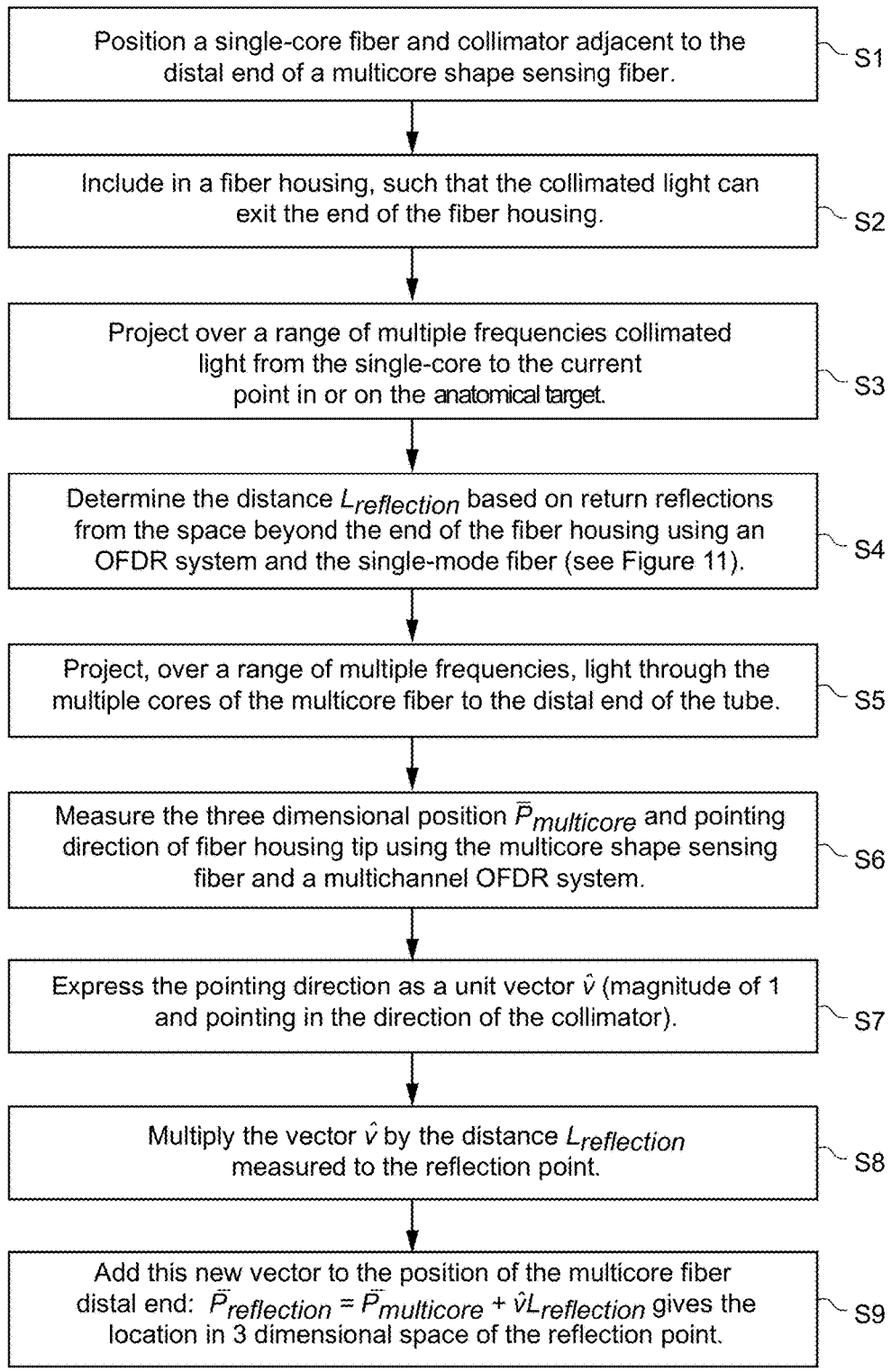
FIG. 12 is a flowchart illustrating example OFDR-based tomography procedures for determining a location in 3-dimensional space of a reflection point in an anatomical target using the fiber pair and an OFDR-based distributed strain measurement system.

FIG. 12 is a flowchart illustrating example OFDR-based tomography procedures for determining a location in 3-dimensional space of a reflection point in an anatomical target using the fiber pair and an example OFDR-based distributed strain measurement system. A single-core fiber and collimator are positioned adjacent to the distal end of a multicore shape sensing fiber (step S1). The fiber pair (of the single-core and multicore fibers) is included in a fiber housing (e.g., a lumen of a catheter), and positioned so that the collimated light can exit the end of the fiber housing towards a current point in or on the anatomical target (step S2). Collimated light is projected over a range of multiple frequencies from the single core to the current point in or on the anatomical target (step S3). A distance $L_{reflection}$ from the tip of the fiber housing to the current point in or on the anatomical target is determined based on return reflections from the end of the fiber housing using an OFDR system and the single-core fiber (see FIG. 11) (step S4). Light is also projected, over a range of multiple frequencies, through the multiple shape sensing cores of the multicore shape sensing fiber to the distal end of the fiber housing (step S5). The three dimensional position $\vec{P}_{multicore}$ and pointing direction of fiber housing tip are measured using the multicore shape sensing fiber and a multichannel OFDR system (step S6). The pointing direction can be expressed as a unit vector $\hat{v}$ (magnitude of 1 and pointing in the direction of the collimator) (step S7). The vector $\hat{v}$ is multiplied by the distance $L_{reflection}$ measured to the reflection point (step S8). This new vector is added to the position of the multicore fiber distal end: $\vec{P}_{reflection} = \vec{P}_{multicore} + \hat{v} L_{reflection}$ and gives the location in 3 dimensional space of the reflection point (step S9). Determining many locations using this procedure maps out the surface of the anatomical target or cavity. If data from beyond the surface of the anatomical target or cavity (the interior of the tissue) is generated, then a tomographic map may be constructed that is a three dimensional description of the subsurface tissue.

Figure 13:
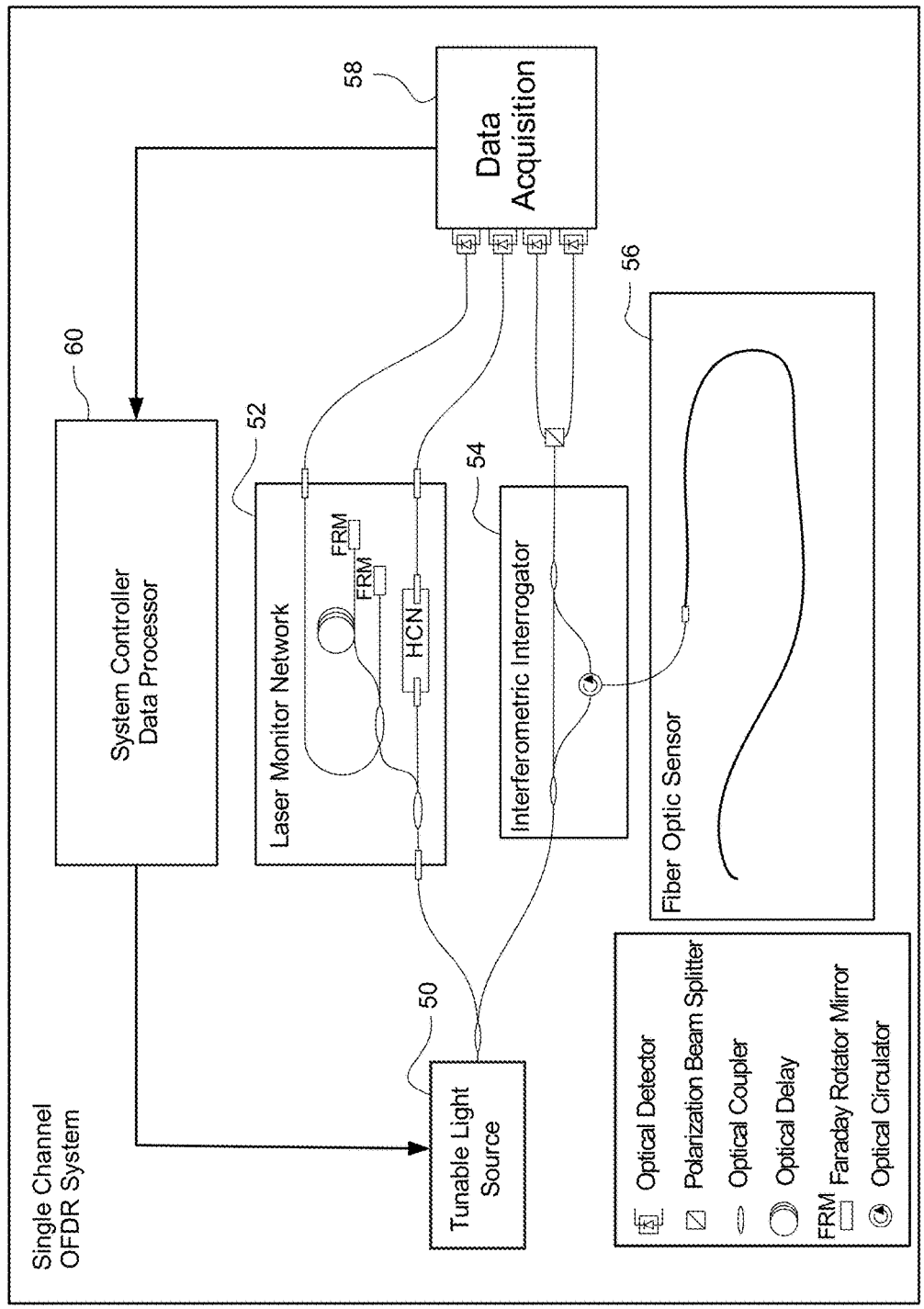
FIG. 13 shows an example OFDR-based distributed strain measurement system.
Figure 14:
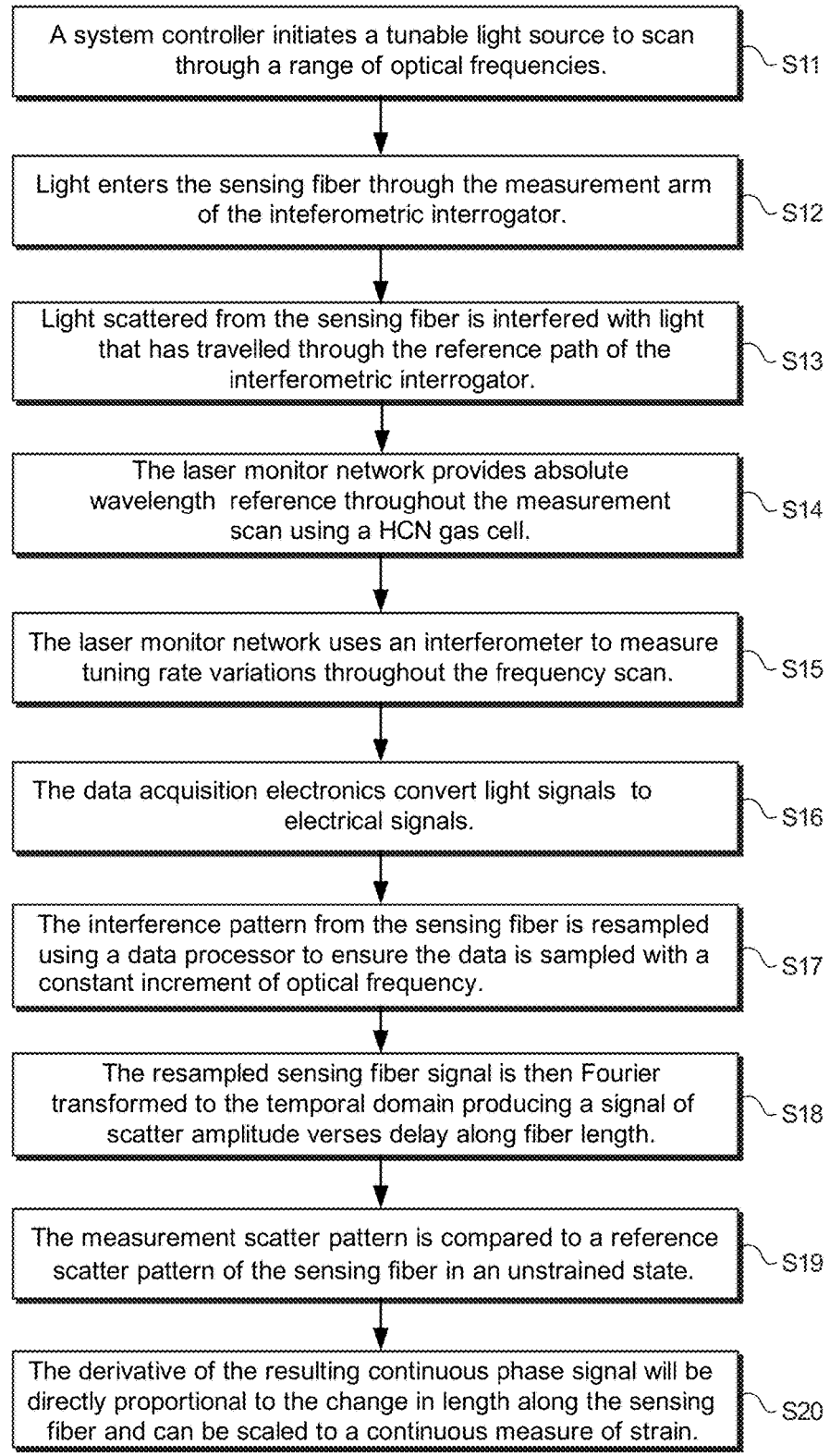
FIG. 14 is a flowchart illustrating example procedures for operating the OFDR-based distributed strain measurement system in FIG. 13.
Figure 15:
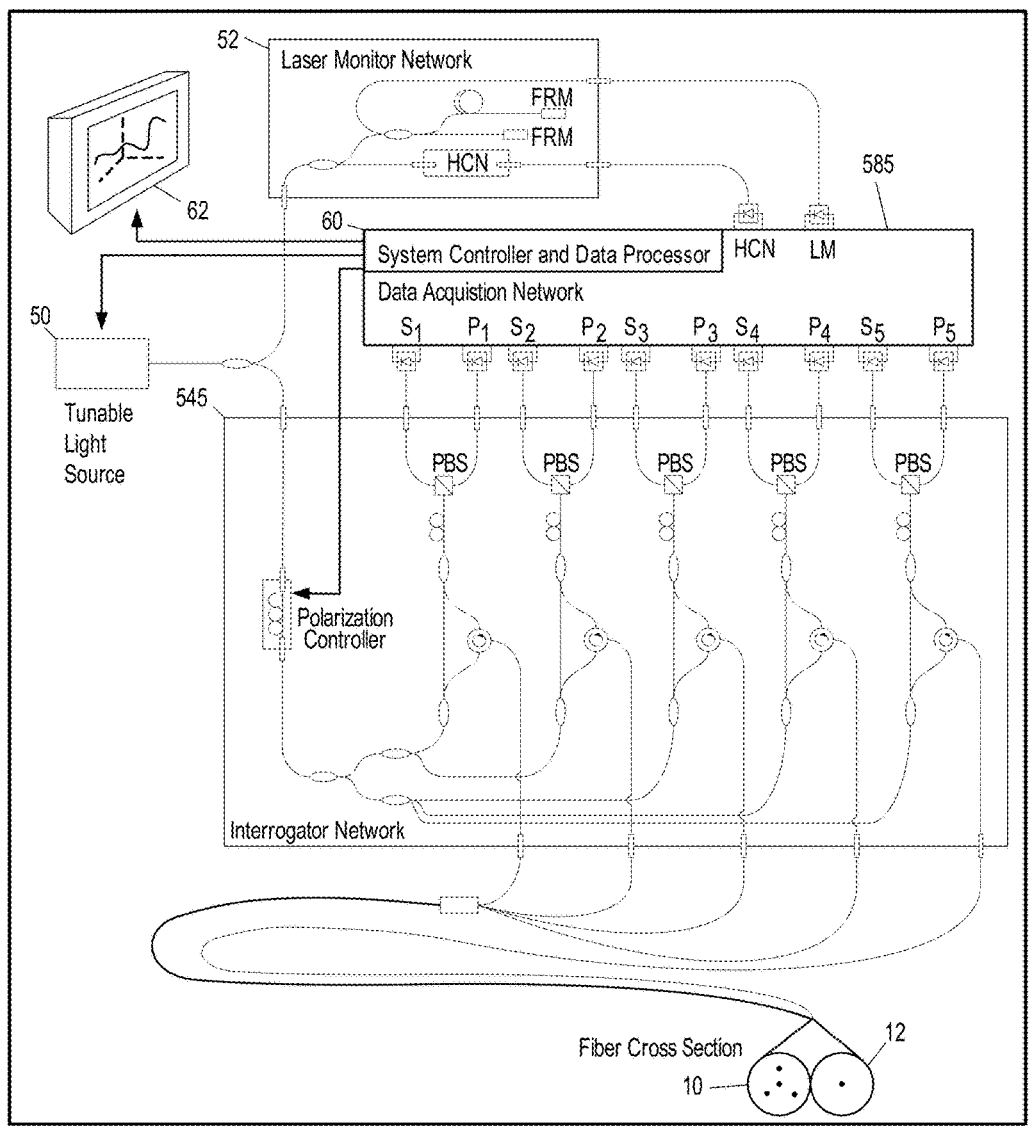
FIG. 15 shows an example reflection-based tomography system.

Some technical description of single channel and multichannel OFDR system operation which are used to implement OFDR-based tomography is now provided in conjunction with FIGS. 13-15. FIG. 13 shows an example single channel OFDR-based distributed measurement system that includes a tunable light source 50 optically coupled to an interferometric interrogator 54 and a laser monitor network 52. A fiber optic sensor comprising a sensing fiber 56 is coupled via a circulator to the measurement arm of the interferometric interrogator 54. The reference and measurement arms of the interferometric interrogator 54 and the outputs from the laser monitor network 52 are coupled to photodiode detectors connected to data acquisition electronics 58. The measurement data is provided from the data acquisition electronics 58 to a system controller data processor 60. A single channel corresponds to a single fiber core.

FIG. 14 is a flowchart illustrating example procedures for operating the OFDR-based distributed measurement system in FIG. 13. During an OFDR measurement, a tunable light source 50 is swept through a range of optical frequencies (step S11). This light is split with the use of optical couplers and routed to two separate interferometers. The first interferometer serves as an interferometric interrogator 54 and is connected to a length of sensing fiber 56. Light enters the sensing fiber 56 through the measurement arm of the interferometric interrogator 54 (step S12). Scattered light from the sensing fiber 56 is then interfered with light that has traveled along the reference arm of the interferometric interrogator 54 (step S13). The laser monitor network 52 contains a Hydrogen Cyanide (HCN) gas cell that provides an absolute wavelength reference throughout the measurement scan (step S14). A second interferometer, within a laser monitor network 52, is used to measure fluctuations in tuning rate as the light source is scanned through a frequency range (step S15). A series of optical detectors (e.g., photodiodes or other optical detectors) convert the light signals from the laser monitor network 52, gas cell, and the interference pattern from the sensing fiber 56 to electrical signals (step S16).

A data processor in a data acquisition unit 58 uses the information from the laser monitor network 52 interferometer to resample the detected interference pattern of the sensing fiber 56 so that the pattern possesses increments constant in optical frequency (step S17). This step is a mathematical requisite of the Fourier transform operation in embodiments. Once resampled, a Fourier transform is performed by the system controller 60 to produce a light scatter signal in the temporal domain (step S18). In the temporal domain, the amplitudes of the light scattering events can be depicted as a function of delay along the length of the fiber.

Using the distance that light travels in a given increment of time, this delay can be converted to a measure of length along the sensing fiber 56. In other words, the light scatter signal indicates each scattering event as a function of distance along the fiber. The sampling period is referred to as the spatial resolution and is inversely proportional to the frequency range that the tunable light source 50 was swept through during the measurement.

As the fiber 56 is strained, the local light scatters shift as part or all of the fiber 56 changes in physical length. These distortions are highly repeatable. Hence, an OFDR measurement of detected light scatter for the fiber 56 can be retained in memory that serves as a reference pattern of the fiber in an unstrained state. A subsequently measured scatter signal when the fiber 56 is under strain may then be compared to this reference pattern by the system controller 60 to gain a measure of shift in delay of the local scatters along the length of the sensing fiber 56 (step S19). This shift in delay manifests as a continuous, slowly varying optical phase signal when compared against the reference scatter pattern. The derivative of this optical phase signal is directly proportional to change in physical length of the sensing core of the sensing fiber 56 (step S20).

Change in physical length is useful to measure a number of different parameters, e.g., it may be scaled to strain producing a continuous measurement of strain along the sensing fiber. The high resolution and high sensitivity required to make these measurements of a fiber core allow the OFDR system to make very sensitive and high resolution measurements of scattering events that take place in media other than optical fibers, such as tissue surfaces and subsurfaces.

FIG. 15 shows an example reflection OFDR-based tomography system which is similar to the single channel OFDR-based distributed sensing system in FIG. 13 but uses multiple channels and a single-core distance/ranging fiber along with a multicore shape sensing fiber. A reflection based OFDR shape sensing system is described in detail in commonly-assigned U.S. Pat. No. 8,773,650, the contents of which are incorporated herein by reference.

Instead of one interferometric interrogator as in FIG. 13, there are four interferometric interrogators referenced generally at 545 corresponding to four core waveguides A, B, C, and D in the fiber. Although the term "core" is used below, the technology applies to other types of waveguides that can be used in a spun fiber. Each of the interferometric interrogators is connected to the tunable light source 50 via optical couplers. Each independent waveguide core within the multi-core optical fiber is then connected to an interferometric interrogator channel. Each pairing of an interferometric interrogator channel with a core in the multi-core fiber 10 or the single-core fiber 12 is referred to as an acquisition channel. As the tunable light source 50 is swept through a range of frequencies, each acquisition channel is simultaneously measured, and the resulting interference pattern from each channel is routed to the data acquisition electronics 585 adapted for the additional interferometers. Each channel is processed independently and identically as described in the flowchart in FIG. 14. The system controller data processor 60 interprets the signals of the four optical cores and produces a measurement of both position and orientation along the length of the shape sensing fiber 10. The measurement data is then exported from the system controller for display 62 and/or other use, such as correlating position for single core fiber 12.

Shape sensing using a multi-core fiber includes detecting a total change in optical length in ones of the cores in the multi-core fiber that reflects an accumulation of all of the changes in optical length for multiple fiber segment lengths up to a point on the multi-core fiber. A location and pointing direction at that point on the multi-core fiber is then determined based on the detected total change in optical length. The data from the single-core fiber channel is processed similarly to the data for each of the shape sensing cores up to the step in which the time-domain response is calculated (S18 in FIG. 14). After this step, the data from the single-core fiber is used to determine the distance to any detected reflection as illustrated in FIG. 11.

Returning to the human or animal anatomical target example described above, if a portion of tissue is observed over time, then motion due to breathing or changes in blood pressure (e.g., due to heart beat) is detectable in some embodiments as relative optical phase shifts in the OFDR signal. Since the interrogator network can perform measurements at rates much higher than breathing or heartbeat rates, these variations can be measured by observing the phase changes through scans and between scans. For example, changes in path-length as small as 70 nm can be measured in some embodiments. Also, measuring OFDR data in both directions of a tunable laser sweep allows detection of relative constant motion (e.g., blood flowing in an artery) due to its Doppler shift. If a reflection is moving toward the source (the tip of the fiber), then the reflection will appear closer than its actual distance when the laser is sweeping up, and the reflection will appear farther than its actual distance when the laser is sweeping down. The scatter pattern from an arterial blood flow, for example, will therefore appear to alternate between two apparent positions, centered about the actual position. By measuring the distance between these two scatter patterns from the up and down scan, and by knowing what the laser sweep rates, the velocity of the scatterer (i.e., the flowing blood) may be calculated.

Figure 16:
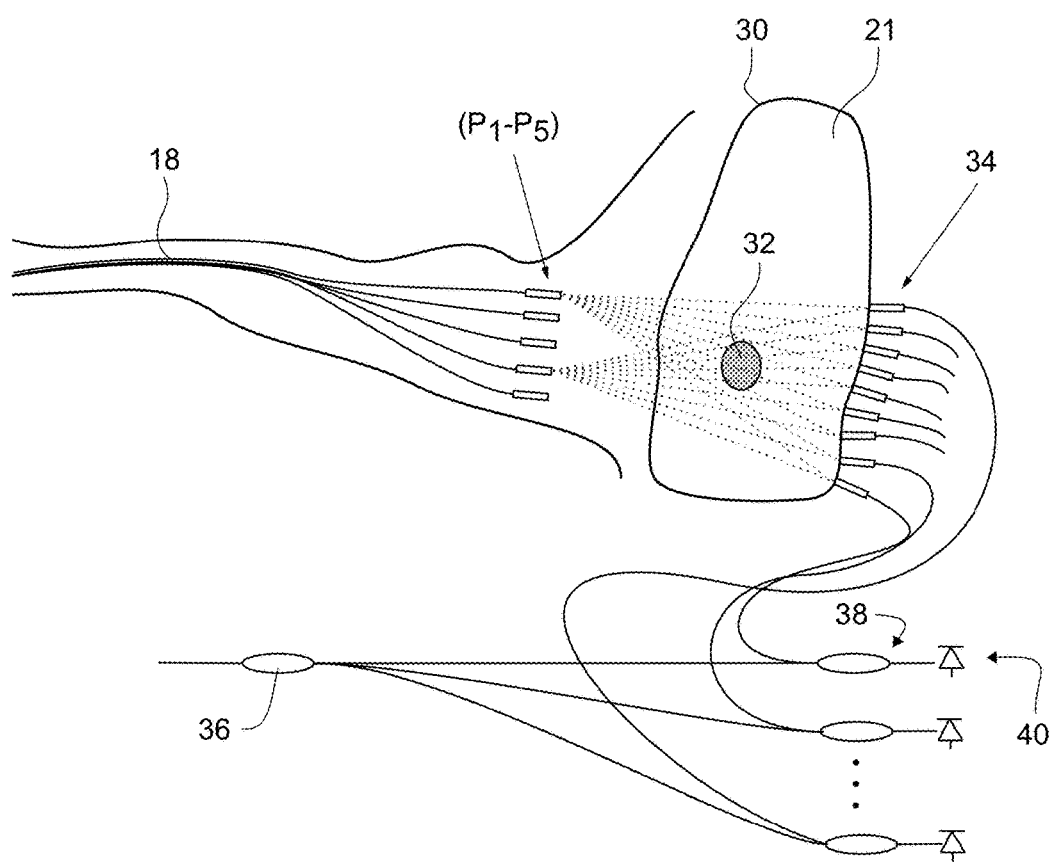
FIG. 16 illustrates an example transmission-based tomography system with multiple detectors.

An example transmission-based tomography embodiment of the technology is now described. FIG. 16 illustrates a simplified example of a transmission-based OFDR tomography system. The fiber housing 18 is inserted into an anatomical target cavity and moved to a plurality of different positions (five are shown as P1-P5). The interior surface 30 of the anatomical target 21 includes a subsurface feature 32. Multiple receiving fibers 34 are shown on the opposite surface or outside the anatomical target. Each receiver fiber 34 can be an individual channel as shown in FIG. 16 where the location is determined using a suitable method. The single-core fiber 12 in the fiber housing 18 functions as a point transmitter. As the fiber housing 18 moves to different positions, light from different origination points P1-P5 travels through the tissue to arrive at one or more of the multiple detecting fibers 34. These detecting fibers 34 collect light into a single-core that then directs the light for OFDR interferometric detection via photodiodes 40. The interferometric detection allows highly sensitive detection of the light and allows the transit time from the single-core fiber 12 to be precisely measured using the swept wavelength processing described in FIG. 14 (S11-S18) except that S13 is changed so that light transmitted from the source fiber to the receiving fiber is interfered with light that has travelled through the reference path of the interrogator. This processing results in measurement of the amplitude and the delay through the path. By measuring the time of flight between the transmitting single-core fiber 12 and each receiving single-core fiber 34, and by knowing the locations of all of the transmitting and receiving positions, the average group index along the path connecting the transmitting fiber 12 and the detecting fibers 34 is measured. The average group index can be calculated by dividing the measured delay between the transmitter and each detector by the delay calculated by dividing the distance between the transmitter and detector by the speed of light in a vacuum. Light that has been multiply scattered can be distinguished from light that takes the direct path to the detector based on the arrival time of the light. By making measurements at multiple locations P1-P5, a three dimensional distribution of the group index of the tissue may be reconstructed.

Figure 17:
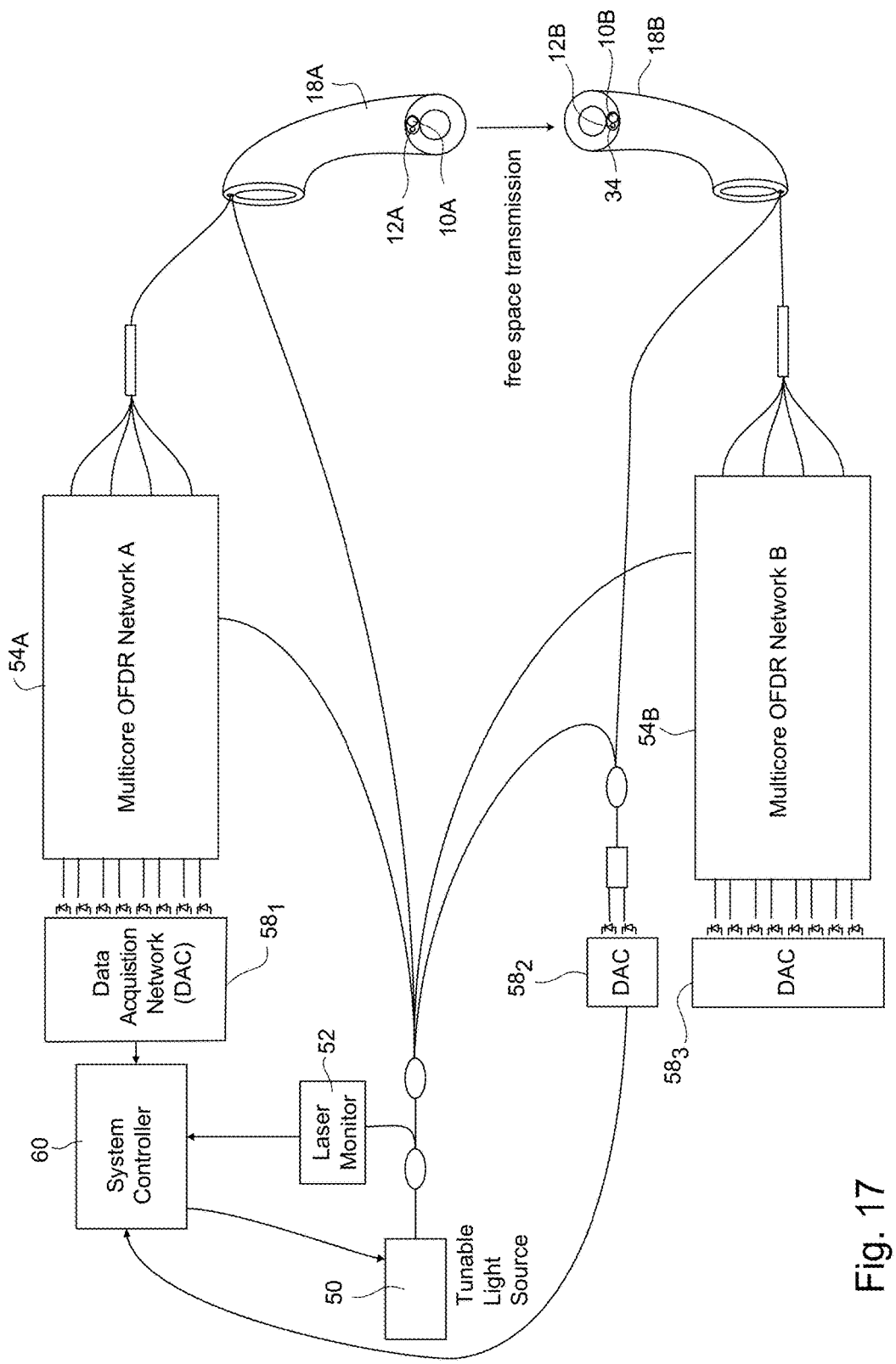
FIG. 17 shows an example single transmitter/single receiver transmission-based tomography system.

FIG. 17 illustrates an example single-transmitter/single-receiver transmission-based tomography system where a single-transmitter/single-receiver fiber pair is moved to different scanning positions. FIG. 17 shows two such single-transmitter/single-receiver pairs. Specifically, FIG. 17 shows two multicore shape sensing networks A and B that share a tunable light source 50, laser monitor network 52, and system controller 60. In addition, there is a single interferometric channel where the transmitter single-core fiber 12A is associated with one multicore shape sensing fiber 10A, and the receiver single-core fiber 12B is associated with the other multicore shape sensing fiber 10B. Because the associated transmitter and receiver fibers remain the same length as their respective tip locations are moved around, any changes in light travel time through the transmitter fibers, the space being probed, and the receiving fibers are due to changes in the time-of-flight between the transmitter and receiver fiber tips.

Figure 18:
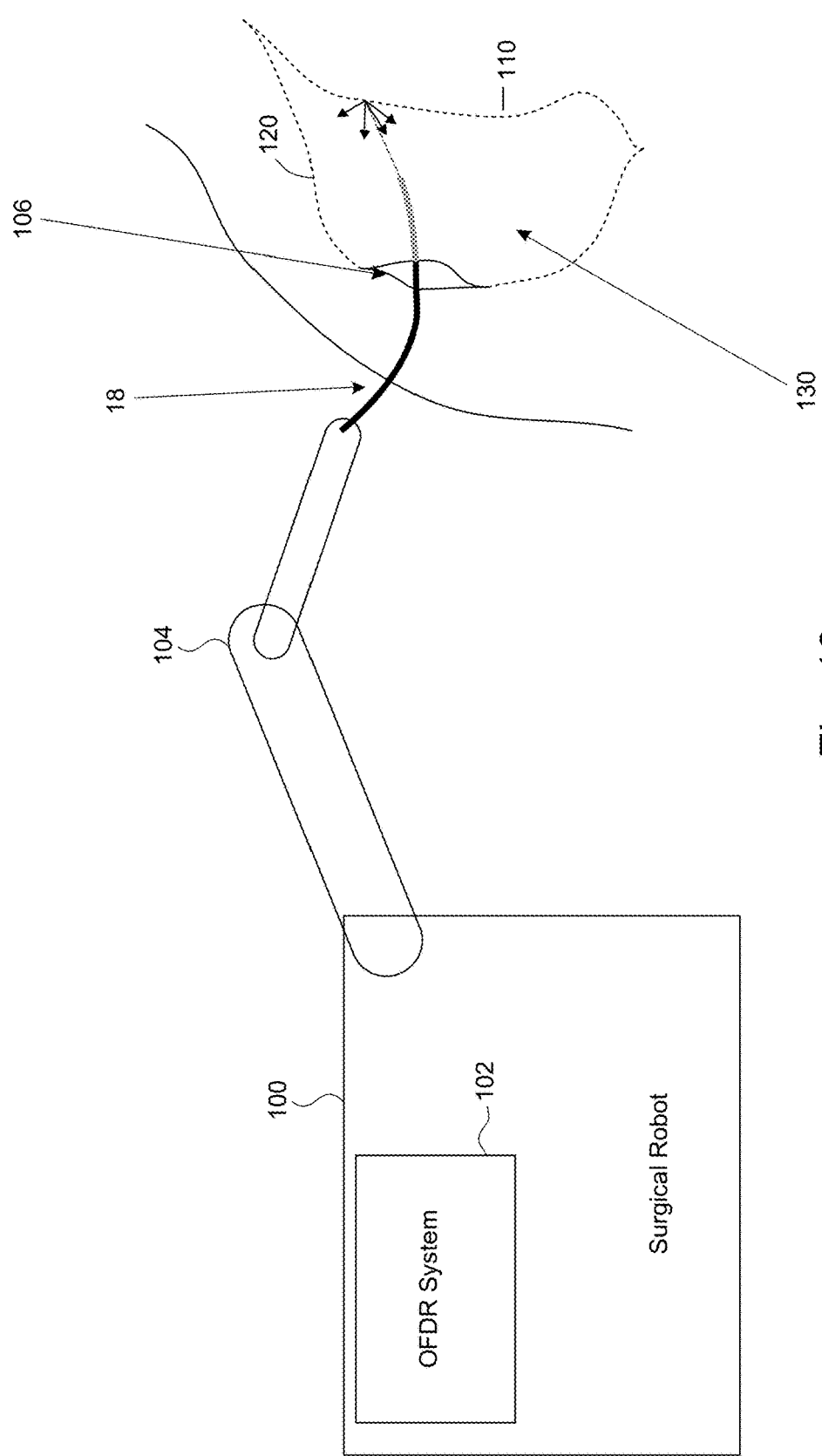
FIG. 18 shows an example surgical robot application of an OFDR-based tomography system.

FIG. 18 shows an example robotic application of an OFDR-based tomography system in a surgical context. A surgical robot 100 includes a robotic arm 104 coupled to fiber housing (e.g., a catheter or other fiber housing) 18 inserted through an incision 106 in an anatomy 120 into an anatomical target cavity 130. The robot 100 includes actuators and control circuitry (not shown) for moving the arm 104 and fiber housing 18 to effect the surgical procedure. The surgeon can control the fiber housing 18 position and pointing direction and, by sweeping the pointing direction of the fiber housing appropriately, map out one or more surfaces, such as surface 110, of the tissue. Alternatively, the scan could be computer controlled and sweep out an orderly raster scan or other scan pattern. In either case, an accurate map of some or all of the dimensions of the cavity 130 can be determined. In some embodiments, subsurface scatter events can measure and present other features not readily visible with normal image techniques to the surgeon or other personnel as overlays.

FIG. 19 shows side and front view of another example application of the OFDR-based tomography technology to determine a location of an anatomical target in space. Here, the exterior surface 1920 of a patient 1910 is measured using one or more OFDR sensing fibers 1930 (three are shown in FIG. 19). Once an accurate measurement of the surface 1920 of the patient's anatomical target is made in a known coordinate system (i.e. the coordinate system that a surgical robot is working in), then previously-taken CAT scans, PET scans, and/or MRI scans can be registered against the measured patient surface 1920 and brought into the known coordinate system. Because infrared light can pass through many textiles, a patient may be clothed and/or under a sheet when these measurements are made.

The above description sets forth specific details, such as particular embodiments for purposes of explanation and not limitation. It will be appreciated by one skilled in the art that other embodiments may be employed apart from these specific details. In some instances, detailed descriptions of well-known methods, nodes, interfaces, circuits, and devices are omitted so as not obscure the description with unnecessary detail. Those skilled in the art will appreciate that the functions described may be implemented in one or more nodes using optical components, electronic components, hardware circuitry (e.g., analog and/or discrete logic gates interconnected to perform a specialized function, ASICs, PLAs, etc.), and/or using software programs and data in conjunction with one or more digital microprocessors or general purpose computers. Moreover, certain aspects of the technology may additionally be considered to be embodied entirely within any form of computer-readable memory, such as, for example, solid-state memory, magnetic disk, optical disk, etc. containing an appropriate set of computer instructions that may be executed by a processor to carry out the techniques described herein.

The term "signal" as used herein to encompass any signal that transfers information from one position or region to another in an electrical, electronic, electromagnetic, optical, or magnetic form. Signals may be conducted from one position or region to another by electrical, optical, or magnetic conductors including via waveguides, but the broad scope of electrical signals also includes light and other electromagnetic forms of signals (e.g., infrared, radio, etc.) and other signals transferred through non-conductive regions due to electrical, electronic, electromagnetic, or magnetic effects, e.g., wirelessly. In general, the broad category of signals includes both analog and digital signals and both wired and wireless mediums. An analog signal includes information in the form of a continuously variable physical quantity, such as voltage; a digital electrical signal, in contrast, includes information in the form of discrete values of a physical characteristic, which could also be, for example, voltage.

Unless the context indicates otherwise, the terms "circuitry" and "circuit" refer to structures in which one or more electronic components have sufficient electrical connections to operate together or in a related manner. In some instances, an item of circuitry can include more than one circuit. A "processor" is a collection of electrical circuits that may be termed as a processing circuit or processing circuitry and may sometimes include hardware and software components. In this context, software refers to stored or transmitted data that controls operation of the processor or that is accessed by the processor while operating, and hardware refers to components that store, transmit, and operate on the data. The distinction between software and hardware is not always clear-cut, however, because some components share characteristics of both. A given processor-implemented software component can often be replaced by an equivalent hardware component without significantly changing operation of circuitry, and a given hardware component can similarly be replaced by equivalent processor operations controlled by software.

Hardware implementations of certain aspects may include or encompass, without limitation, digital signal processor (DSP) hardware, a reduced instruction set processor, hardware (e.g., digital or analog) circuitry including but not limited to application specific integrated circuit(s) (ASIC) and/or field programmable gate array(s) (FPGA(s)), and (where appropriate) state machines capable of performing such functions.

Circuitry can be described structurally based on its configured operation or other characteristics. For example, circuitry that is configured to perform control operations is sometimes referred to herein as control circuitry and circuitry that is configured to perform processing operations is sometimes referred to herein as processing circuitry.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed.

Although various embodiments have been shown and described in detail, the claims are not limited to any particular embodiment or example. None of the above description should be read as implying that any particular element, step, range, or function is essential such that it must be included in the claims scope. The scope of patented subject matter is defined only by the claims. The extent of legal protection is defined by the words recited in the allowed claims and their equivalents. All structural and functional equivalents to the elements of the above-described embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC § 112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. A method of operating an interferometric system to use multiple shape-sensing optical cores and a single optical core in a fiber housing to generate a three-dimensional data set for at least a portion of a target based on distance measurements of multiple points of the target from a distal end of the fiber housing and measurements of respective three-dimensional positions of the distal end, the multiple shape-sensing cores located alongside the single optical core, the method comprising:
  (a) projecting, over a first range of multiple frequencies, collimated light from the single optical core to a current point of the target while the distal end of the fiber housing is directed toward the current point;
  (b) using optical frequency domain reflectometry to detect reflected light scattered from the current point and to process the reflected light to determine a distance of the distal end to the current point;
  (c) projecting, over a second range of multiple frequencies, light through the multiple shape-sensing optical cores to the distal end of the fiber housing;
  (d) using optical frequency domain reflectometry to obtain a measurement of light reflected from the distal end of the fiber housing back through the multiple shape-sensing optical cores and to process the measurement to determine a position in three-dimensional space of the distal end of the fiber housing and a pointing direction of the distal end of the fiber housing;
  (e) using the determined position in three-dimensional space of the distal end of the fiber housing, the pointing direction of the distal end of the fiber housing, and the determined distance to determine a position in three-dimensional space of the current point; and
  repeating (a)-(e) multiple times for multiple additional current points of the target to generate the three-dimensional data set for at least the portion of the target,
  wherein, to generate the three-dimensional data set, the single optical core is used only to determine distances of the distal end to the multiple points of the target, and wherein generating the three-dimensional data set requires combining the distances with the respective three-dimensional positions of the distal end.

2. The method in claim 1, further comprising:
  expressing the pointing direction of the distal end of the fiber housing as a unit vector pointing in a direction of the distal end of the fiber housing along a pointing axis;
  multiplying the unit vector by the determined distance to generate a reflection distance vector; and
  combining the determined position in three-dimensional space of the distal end of the fiber housing with the reflection distance vector to generate the determined position in three-dimensional space of the current point in or on the target.

3. The method in claim 1, further comprising generating a tomographical map of at least a portion of a surface of the target based on the three-dimensional data set.

4. The method in claim 1, further comprising generating a tomographical map of at least a portion of the target beneath a surface of the target based on the three-dimensional data set.

5. The method in claim 1, further comprising using the three-dimensional data set to provide navigation guidance relative to the target.

6. The method in claim 1, further comprising:
  detecting relative optical phase shifts in the reflected light caused by motion of the target and compensating the three-dimensional data set for motion of the target based on the detected relative optical phase shifts.

7. The method in claim 1, further comprising:
  determining a position in three-dimensional space of points on an outside of the target to determine a location of the target in three-dimensional space, and
  using the determined location of the target in three-dimensional space and a radiation-based scan of the target to determine a location of one or more structures inside the target in three-dimensional space.

8. An interferometric measurement system for generating a three-dimensional data set for at least a portion of an anatomical target based on distance measurements of multiple points of the target from a distal end of a fiber housing and measurements of respective three-dimensional positions of the distal end, the system comprising:
  the fiber housing and, contained in the fiber housing, multiple shape-sensing optical cores and a single optical core alongside the multiple shape-sensing optical cores, the fiber housing being positionable to direct the single optical core to a current point of the anatomical target;
  a tunable light source configured to (a) project, over a first range of multiple frequencies, light through the single optical core and a collimator to the current point; and
  circuitry configured to (b) detect reflected light scattered from the current point and to process the reflected light to determine a distance of the distal end of the fiber housing to the current point using optical frequency domain reflectometry (OFDR);
  the tunable light source being further configured to (c) project, over a second range of multiple frequencies, light through the multiple shape-sensing optical cores to the distal end of the fiber housing;
  the circuitry being further configured to (d) measure light reflected from the distal end of the fiber housing back through the multiple shape-sensing optical cores and to (e) process the measured light to determine a position in three-dimensional space of the distal end of the fiber housing and a pointing direction of the distal end of the fiber housing using OFDR;
  the circuitry being further configured to (f) determine a position in three-dimensional space of the current point based on the determined position in three-dimensional space of the distal end of the fiber housing, the pointing direction of the distal end of the fiber housing, and the determined di stance,
  wherein the tunable light source and the circuitry are configured to perform respective ones of (a)-(f) multiple times to generate the three-dimensional data set for at least the portion of the anatomical target, wherein the single optical core is used only to determine distances of the distal end to the multiple points of the target, and wherein generating the three-dimensional data set requires combining the distances with the respective three-dimensional positions of the distal end.

9. The interferometric measurement system in claim 8, wherein the circuitry is further configured to:
  express the pointing direction of the distal end of the fiber housing as a unit vector pointing in a direction of the distal end of the fiber housing along a pointing axis;

multiply the unit vector by the determined distance to generate a reflection distance vector; and combine the determined position in three-dimensional space of the distal end of the fiber housing with the reflection distance vector to generate the determined position in three-dimensional space of the current point.

10. The interferometric measurement system in claim 8, wherein the circuitry is further configured to process a time delay from a reflection at the collimator to a first reflection scattered from the current point as an indication of the distance from the distal end of the fiber housing to the current point.

11. The interferometric measurement system in claim 8, wherein the multiple cores and the single core are in a same fiber.

12. The interferometric measurement system in claim 8, wherein the multiple shape-sensing cores and the single core are in different fibers, and wherein the different fibers are fixed in a known positional relationship with each other.

13. The interferometric measurement system in claim 8, further comprising:

an actuator configured to direct the distal end of the fiber housing at a second current point of the anatomical target.

14. The interferometric measurement system in claim 8, wherein the three-dimensional data set provides information about a distribution of tissue of an area in the anatomical target.

15. The interferometric measurement system in claim 8, wherein the circuitry is configured to generate a tomographical map of at least a portion of a surface of the anatomical target based on the three-dimensional data set.

16. The interferometric measurement system in claim 8, wherein the circuitry is configured to generate a tomographical map of at least a portion of the anatomical target beneath a surface of the anatomical target based on the three-dimensional data set.

17. The interferometric measurement system in claim 8, wherein the circuitry is configured to:

determine a position in three-dimensional space of points on an outside of the anatomical target to determine a location of the anatomical target in three-dimensional space, and use the determined location of the anatomical target in three-dimensional space and a radiation-based scan of the anatomical target to determine a location of one or more structures inside the anatomical target in three-dimensional space.

18. The interferometric measurement system in claim 8, wherein the circuitry is configured to detect relative optical phase shifts in the reflected light caused by motion of anatomical target tissue and compensate the three-dimensional data set for motion of anatomical target tissue based on the relative optical phase shifts.

19. A non-transitory machine-readable medium comprising a plurality of machine-readable instructions which when executed by one or more processors associated with a medical device are adapted to cause the one or more processors and the medical device, under control of the one or more processors, to perform a method for generating a three-dimensional data set for at least a portion of a target based on distance measurements of multiple points of the target from a distal end of a fiber housing and measurements of respective three-dimensional positions of the distal end, the medical device comprising the fiber housing and, located in the fiber housing alongside each other, a single optical core and multiple shape-sensing optical cores, the method comprising the steps of:

(a) projecting, over a first range of multiple frequencies, collimated light from the single optical core to a current point of the target, while the distal end of the fiber housing is directed toward the current point;

(b) using optical frequency domain reflectometry to detect reflected light scattered from the current point and to process the reflected light to determine a distance of the distal end to the current point;

(c) projecting, over a second range of multiple frequencies, light through the multiple shape-sensing optical cores to the distal end of the fiber housing;

(d) using optical frequency domain reflectometry to obtain a measurement of light reflected from the distal end of the fiber housing back through the multiple shape-sensing optical cores and to process the measurement to determine a position in three-dimensional space of the distal end of the fiber housing and a pointing direction of the distal end of the fiber housing;

(e) using the determined position in three-dimensional space of the distal end of the fiber housing, the pointing direction of the distal end of the fiber housing, and the determined distance to determine a position in three-dimensional space of the current point; and repeating steps (a)-(e) multiple times for multiple additional current points of the target to generate the three-dimensional data set for at least the portion of the target, wherein the single optical core is used only to determine distances of the distal end to the multiple points of the target, and wherein generating the three-dimensional data set requires combining the distances with the respective three-dimensional positions of the distal end.

20. The non-transitory machine-readable medium of claim 19, wherein the steps further comprise detecting relative optical phase shifts in the reflected light caused by motion of the target, and compensating the three-dimensional data set for motion of the target based on the relative optical phase shifts.

* * * * *

UNITED STATES PATENT AND TRADEMARK OFFICE
CERTIFICATE OF CORRECTION

PATENT NO. : 10,480,926 B2
APPLICATION NO. : 15/757436
DATED : November 19, 2019
INVENTOR(S) : Froggatt et al.

Page 1 of 1

It is certified that error appears in the above-identified patent and that said Letters Patent is hereby corrected as shown below:

In the Claims

In Column 14, Line 53, in Claim 8, delete "di stance," and insert --distance,-- therefor Signed and Sealed this
Twenty-first Day of April, 2020

Andrei Iancu
*Director of the United States Patent and Trademark Office*